United States Patent [19]

Norton et al.

[11] 4,270,014
[45] May 26, 1981

[54] PRODUCTION OF HIGH ENERGY FUEL

[75] Inventors: Richard V. Norton, Dublin; Steven C. Howe, Columbus, both of Ohio

[73] Assignee: Ashland Oil, Inc., Ashland, Ky.

[21] Appl. No.: 34,879

[22] Filed: Apr. 30, 1979

[51] Int. Cl.$^2$ ............................................. C07C 13/28
[52] U.S. Cl. ..................................... 585/22; 585/360; 585/14; 585/353; 585/253; 60/208
[58] Field of Search .................................. 585/360, 22

[56] References Cited

U.S. PATENT DOCUMENTS 3,381,046  4/1968  Cohen et al. ............................ 585/22
4,086,284  4/1978  Schneider et al. .................... 585/360

Primary Examiner—Veronica O'Keefe

[57] ABSTRACT

A method for converting endo-tetrahydrodicyclopentadiene to the corresponding exo isomeric form which is advantageously carried out in the presence of aluminum chloride catalyst and the spent nickel hydrogenation catalyst utilized in hydrogenating an endo dimer of cyclopentadiene to provide said tetrahydro derivative thereof.

5 Claims, No Drawings

PRODUCTION OF HIGH ENERGY FUEL

BACKGROUND OF THE INVENTION

1. Field of the Invention

This invention relates to a process for catalytically effecting the stereochemical isomerization of tetrahydrodicyclopentadiene.

2. Description of the Prior Art

A hydrocarbon fuel for jet propelled, limited-volume systems; e.g., missiles, must exhibit a requisite combination of properties in order to be useful for this purpose. Foremost, the fuel should possess a high density and a corresponding high heat of combustion. Additionally it is required that such high energy fuels have a low freezing point and exceptional chemical stability.

A hydrocarbon composition meeting the foregoing requirements represents a complex chemical structure which, in general, must be paintakenly synthesized. A high energy fuel of this type is exemplified by exo-tetrahydrodicyclopentadiene (exo-THDCPD) which has been adopted by the U.S. Air Force for certain jet propelled systems and accordingly designated JP-10. The procedure involved for producing JP-10 consists of first dimerizing cyclopentadiene followed by completely hydrogenating the resultant dimer to provide the endo stereo isomeric form of the tetrahydro derivative.

Endo-THDCPD is unsuitable as a fuel per se because of the compound's high melting point; i.e., 77° C. Accordingly, to obtain JP-10, the endo isomeric precursor is converted to its exo form having a freezing point of about −79° C. This isomerization step represents the most critical part of the overall synthesis procedure in that it is comparatively fraught with difficulties. In U.S. Pat. No. 3,381,046 it is taught that the indicated isomerization can be effected through the agency of a strong acid catalyst. Representative of such catalysts include strong Brönsted and Lewis acids. The Brönsted acids, such as the preferred acid; viz.; sulfuric acid, suffer in that the resultant conversion yields are economically unacceptable for commercial production. The use of a strong Lewis acid, on the other hand, is prone to cause the isomerization reaction to proceed beyond the exo isomer thereby resulting in the objectionable formation of substantial amounts of transdecalin and adamantane.

Subsequent workers in this field have proposed that aluminum chloride can be effectively utilized as an isomerization catalyst while minimizing the difficulties referred to in the above-mentioned prior art provided the isomerization reaction temperature is carefully controlled. U.S. Pat. No. 4,086,284 is exemplary of this prior art. The latter teaches that the isomerization temperature is not to exceed 90° C. and more preferably is in the order of about 70° C. in order to avoid the formation of transdecalin and adamantane and to prevent an uncontrolled exotherm from occurring. The foremost disadvantage of this method of operation resides in the commercially intolerable conversion rates that are applicable. Moreover, this disadvantage is exacerbated by the fact that the presence of an inert solvent is practically necessitated because of physical handling difficulties encountered in carrying out the reaction at the relatively low temperatures specified.

SUMMARY OF THE INVENTION

In accordance with the present invention a process is provided for efficiently and essentially completely converting endo-THDCPD to the exo isomeric form thereof through the agency of aluminum chloride as the isomerization catalyst. The gist of the invention resides in the discovery that aluminum chloride will provide the indicated improved results provided that the isomerization reaction is carried out in the presence of the spent nickel hydrogenation catalyst utilized in obtaining said endo-THDCPD.

DESCRIPTION OF THE PREFERRED EMBODIMENTS

While the relevant prior art embraces a variety of metal hydrogenation catalysts for use in effecting the hydrogenation of endo-dicyclopentadiene, the practice of this invention contemplates the use of an applicable nickel catalyst. The amount of catalyst applicable for this purpose is in the order of 1–1.5 weight percent catalyst based on the charge of the DCP. Otherwise, the preferred procedure of the prior art for carrying out hydrogenation is applicable in implementing the invention. This procedure involves carrying out the hydrogenation in two stages. In the first stage the 8, 9 positions of the dimerized product are hydrogenated at a temperature generally in the order of about 120° C. The dihydro derivative is relatively thermally stable thus permitting the use of a substantially higher temperature in the second stage; viz., in the order of about 215° C. Hydrogenation is carried out in the second stage to the extent whereby the resultant product exhibits a melting point of at least about 70° C. Adequate hydrogen concentration is obtained during hydrogenation under moderate pressure conditions ranging from about 5 to 15 atmospheres. Representative hydrogenation runs will be illustrated in the working example presented hereinbelow.

The crude hydrogenation product is utilized as such in the subsequent isomerization step although, if desired, the product can be distilled in order to remove residual olefinic material for recycling purposes. The isomerization is then carried out in the presence of aluminum chloride catalyst which, if used in the anhydrous form, is employed in an amount ranging from about 0.5–5.0 weight percent based on endo-THDCPD charge and more preferably, in the order of 1–3 weight percent. As is the case in typical alkylation reactions conducted in the presence of aluminum chloride, it appears that the actual catalyst values are the complexes formed between the aluminum chloride and the hydrocarbon substrate during the course of reaction. These complexes are conventionally referred to as an aluminum chloride sludge. Accordingly, the sludge upon enrichment with fresh aluminum chloride can advantageously be utilized over and over again resulting in a substantial overall reduction of expensive aluminum chloride usage.

As indicated previously the practice of this invention desirably allows one to observe a substantially higher reaction temperature than that heretofore recommended. The applicable range of reaction temperature is accordingly from about 100°–150° C. Operating within this range facilitates intimate mixing of the reaction mixture thereby providing improved conversion rates. Although not required, an inert solvent can be employed to further facilitate mixing in the initial part of the reaction. While a variety of solvents can be used in this manner, the preferred solvent is preformed exo-THDCPD.

The extent of conversion to the exo isomer can be conveniently monitored by vapor liquid gas chromatography. Upon attaining substantially complete conversion, i.e., 98±%, the reaction mixture is preferably cooled to about 80° C. to provide upon settling a two-phase system having a sharp meniscus thereby permitting facile recovery of the fuel from the sludge by simple decantation. Optionally, separation of the phases can be accomplished without observing the indicated cooling step if a high temperature centrifuge or filtration means is available.

In order to further illustrate the invention the following working example is provided in which are parts and percentages referred to therein are by weight unless otherwise indicated.

EXAMPLE I

Commercial dicyclopentadiene was hydrogenated using Girdler G-49-B nickel catalyst on a pilot plant scale in a pressure vessel having a capacity of 250 gallons. Further details regarding the processing conditions observed and results obtained for several representative runs are outlined in the following Table I.

TABLE I

| Run No. | DCP Charge (#) | Wt. % Cat. | Hydrogen,-1st Stage Temp. (°C.) | Press. (psig) | Time (hrs) | Hydrogen,-2nd Stage Temp. (°C.) | Press. (psig) | Time (hrs) | Wt. of Final Product (#) | % endo-THDCPD in Final Prod. | % Yield | Melting Point (°C.) |
|---|---|---|---|---|---|---|---|---|---|---|---|---|
| I | 1334 | 1.33 | 95 | 100 | 4.5 | 180 | 150 | 2.0 | 1314 | 97.5 | 96.1 | 68 |
| II | 890 | 1.22 | 100 | 150 | 3.0 | 160 | 150 | 2.5 | 856 | 96.5 | 92.9 | 69.5 |
| III | 1113 | 0.98 | 108 | 150 | 3.5 | 205 | 150 | 2.5 | 1060 | 96.3 | 90.9 | 68 |

The following runs are illustrative of the manner for isomerizing endo-THDCPD to the exo isomer in accordance with the present invention. In each run the crude endo-THDCPD contained the spent nickel catalyst utilized in the hydrogenation reaction. The general procedure involved consisted of heating the crude hydrogenation product to a molten state thereupon adding the aluminum chloride catalyst and permitting the exothermic heat of reaction to effect an adiabatic rise in the reaction temperature. Further reaction details and the results obtained are given in the following Table II.

TABLE II

| Run No. | Endo-THDCPD Charge-lbs. | Wt. % AlCl₃ | Initial Temp.-°C. | Final Temp.-°C. | Reaction Time-Hrs. |
|---|---|---|---|---|---|
| IV | 1303 | 0.7 | 72 | 107 | 4 |
| V | 1170 | 1.4 | 95 | 124 | 3 |
| VI | 1102 | 2.2 | 68 | 121 | 3 |

| | Final Isomerization Product | | | | |
|---|---|---|---|---|---|
| | Total Wt. | % Exo | % Endo | % Admantane | % Yield | % Conversion of Endo-THDCPD |
| IV | 1053 | 97.8 | 1.7 | 0.5 | 81 | 98.6 |
| V | 1078 | 97.3 | 2.1 | 0.6 | 92 | 98.0 |
| VI | 1092 | 97.1 | 2.0 | 0.9 | 99 | 98.0 |

What is claimed is:

1. A process for the production of exo-tetrahydrodicyclopentadiene which comprises:
   (a) hydrogenating the endo dimer of cyclopentadiene containing a dispersed nickel hydrogenation catalyst to provide a crude endo-tetrahydrodicyclopentadiene derivative having a melting point of at least about 70° C,;
   (b) contacting the crude product of (a) containing said catalyst with aluminum chloride and maintaining the contacted crude at a temperature of from about 100°–150° C. to effect the substantially complete conversion of said endo isomer to the corresponding exo isomer form; and
   (c) separating said exo isomer from the sludge component of the isomerization reaction mixture.

2. A process in accordance with claim 1 wherein the hydrogenation is initially conducted at a temperature of from about 110°–120° C. to effect substantially complete hydrogenation of the 8 and 9 positions of said endo dimer and whereupon the hydrogenation is completed at a temperature of from about 150°–200° C.

3. A process in accordance with claim 2 wherein said isomerization reaction is effected in the presence of an inert solvent.

4. A process in accordance with claim 3 wherein said inert solvent comprises added exo-tetrahydrodicyclopentadiene.

5. A process in accordance with claim 2 wherein the crude endo-tetrahydrodicyclopentadiene is contacted in the isomerization reaction with aluminum chloride enriched sludge.

* * * * *